US009510907B2

(12) United States Patent
Liu et al.

(10) Patent No.: US 9,510,907 B2
(45) Date of Patent: Dec. 6, 2016

(54) BILATERAL COOLING TYPE SEMICONDUCTOR LASER SYSTEM FOR MEDICAL BEAUTY USE

(71) Applicant: Xi'An Focuslight Technologies Co., Ltd., Xi'An, Shanxi (CN)

(72) Inventors: Xingsheng Liu, Xi'An (CN); Ye Dai, Xi'An (CN); Yao Sun, Xi'An (CN); Di Wu, Xi'An (CN); Hengjun Zong, Xi'An (CN); Lishun Tong, Xi'An (CN); Lei Cai, Xi'An (CN)

(73) Assignee: Focuslight Technologies Inc, Shaanxi Xi'an (CN)

( * ) Notice: Subject to any disclaimer, the term of this patent is extended or adjusted under 35 U.S.C. 154(b) by 49 days.

(21) Appl. No.: 14/646,436

(22) PCT Filed: Nov. 21, 2013

(86) PCT No.: PCT/CN2013/087590

§ 371 (c)(1),
(2) Date: May 21, 2015

(87) PCT Pub. No.: WO2014/079374

PCT Pub. Date: May 30, 2014

(65) Prior Publication Data

US 2015/0313671 A1 Nov. 5, 2015

(30) Foreign Application Priority Data

Nov. 22, 2012 (CN) .......................... 2012 1 0479917
Nov. 22, 2012 (CN) .......................... 2012 1 0480599

(51) Int. Cl.
*A61B 18/20* (2006.01)
*G02B 6/42* (2006.01)
(Continued)

(52) U.S. Cl.
CPC ............. *A61B 18/20* (2013.01); *A61B 18/203* (2013.01); *A61N 5/0617* (2013.01);
(Continued)

(58) Field of Classification Search
CPC .. H01S 5/02423; H01S 5/405; H01S 5/02415; A61N 2005/067; A61N 5/0617; A61B 18/20; A61B 6/4268; A61B 6/4206; A61B 18/203; A61B 2018/2065; A61B 2018/00023; A61B 2018/00452; A61B 2018/00476
See application file for complete search history.

(56) References Cited

FOREIGN PATENT DOCUMENTS

CN 1452465 * 10/2003 ............ A61B 18/20

* cited by examiner

*Primary Examiner* — Gary Jackson
*Assistant Examiner* — Scott T Luan
(74) *Attorney, Agent, or Firm* — Na Xu; IPro, PLLC

(57) ABSTRACT

Disclosed is a bilateral cooling type semiconductor laser system for medical beauty use, the contact window of which can make direct contact with the skin. The bilateral cooling type semiconductor laser system for medical beauty use comprises a semiconductor laser array, an optical waveguide located on the front end of the light emitting surface of the semiconductor laser array, a transparent contact window abutting against the light outlet end of the optical wave-guide, a pair of cooling blocks and a first water throughflow block. The first water throughflow block is divided into a basal part and a U-shaped head located above the basal part, and the middle part and back part of the optical waveguide are embedded in the U-type header. A fixed block is provided above the corresponding optical waveguide to press and fix the optical waveguide. There is still a space between the optical waveguide and the side wall of the U-type header. The pair of cooling blocks extends to the forepart of the optical waveguide and encircles the side wall of the contact
(Continued)

window and the forepart of the optical waveguide. The system uses a unique cooling structure design, so that the temperature of the working end face which is in direct contact with the skin can be close to freezing point, and the system has a compact and stable structure.

13 Claims, 2 Drawing Sheets

(51) Int. Cl.
*A61N 5/06* (2006.01)
*A61B 18/00* (2006.01)
*H01S 5/024* (2006.01)
*A61N 5/067* (2006.01)
*H01S 5/40* (2006.01)

(52) U.S. Cl.
CPC ......... *G02B 6/4206* (2013.01); *G02B 6/4268* (2013.01); *A61B 2018/00023* (2013.01); *A61B 2018/00452* (2013.01); *A61B 2018/00476* (2013.01); *A61B 2018/2065* (2013.01); *A61N 2005/067* (2013.01); *H01S 5/02415* (2013.01); *H01S 5/02423* (2013.01); *H01S 5/405* (2013.01)

BILATERAL COOLING TYPE SEMICONDUCTOR LASER SYSTEM FOR MEDICAL BEAUTY USE

FIELD OF THE INVENTION

The invention relates to the use of a semiconductor laser, and more particularly to a bilateral cooling type semiconductor laser system for medical beauty use.

BACKGROUND OF THE INVENTION

As an important application field of laser, laser medical treatment has developed quickly in recent years and gradually matured. Featuring small size, light weight, long service life, low power consumption, broad wavelength coverage, etc., semiconductor lasers are particularly suitable for the manufacturing of medical facilities.

Typical laser hair removal facilities include ruby laser (wavelength of 694 nm), alexandrite laser (wavelength of 755 nm), semiconductor laser (wavelength of 810 nm), and Q-switched Nd YAG laser (wavelength of 1064 nm), among which, the semiconductor laser has been proved as a safe and effective hair removal tool.

It is estimated that in 2010 there are about 5 million person times of laser hair removal surgery all over the world. Another important application of the semiconductor laser in the beauty field is to conduct skin renewal, that is, for wrinkle removal and skin rejuvenation. Laser is absorbed by moisture in the dermal collagen tissue to produce thermal effect, which stimulates the regeneration and remolding of collagen thereby smoothing and softening the skin, and providing the skin with elasticity. In addition, laser can also be used for treatment of dark, blue pigment lesions such as freckles, traumatic pigmentation, tattoo removal, eyebrow, eyeliner, and the like.

The most widely used thermal source in ophthalmology is the semiconductor laser, which can be used for treatment of refractory glaucoma, refractory intraocular hypertension after silicon oil injection, and photocoagulation and fixation of retina, and the like.

With the development and maturation of the semiconductor laser technology, the semiconductor laser exhibits more and more advantages and the application scope thereof is expanding rapidly, almost covering the application scopes of all other lasers. The semiconductor laser can not only make up for the shortcomings of difficult optical fiber transmission and inconvenient operation of a high energy $CO_2$ laser, but also make up for the shortcomings of low efficiency and inconvenient heat dissipation of a lamp pumped solid laser, so it is a potential mainstream medical laser.

Chinese Patent No. CN1452465 discloses a laser hair removal device from Yama Ltd., Japan. The device employs a semiconductor laser with an output power of 5 mW-1500 mW and a wavelength of 600 nm-1600 nm for hair removal. However, the system has a low output power, small spot size, and nonadjustable output wavelength, so the hair removal efficiency is very low.

SUMMARY OF THE INVENTION

In view of the above-described problems, it is one objective of the invention to provide a bilateral cooling type semiconductor laser system for medical beauty use. The contact window of the system can contact skin directly.

The object of the present disclosure is achieved by the following technical solution.

To achieve the above objective, in accordance with one embodiment of the invention, there is provided a bilateral cooling type semiconductor laser system, comprising: a semiconductor laser array comprising a plurality of stacked semiconductor lasers, an optical waveguide disposed in front of a light emitting surface of the semiconductor laser array, a transparent contact window abutting against a light outlet end of the optical waveguide, a pair of cooling blocks for conduction cooling of the contact window, and a first water throughflow block. The semiconductor laser array is disposed on the second water throughflow block and an insulating barrier is disposed therebetween; the first water throughflow block comprises a base and a U-shaped head located on the base; middle and rear parts of the optical waveguide are embedded in the U-shaped head; a fixed block is disposed on a corresponding part of the optical waveguide to tightly press and fix the optical waveguide; a gap is provided between the optical waveguide and side walls of the U-shaped head; a pair of thermoelectric coolers (TEC) and a pair of cooling blocks are sequentially and symmetrically disposed at outer sides of the U-shaped head; the pair of cooling blocks extends to a forepart of the optical waveguide and encircles side walls of the contact window and the forepart of the optical waveguide.

Based on the above-mentioned basic technical scheme, the present invention also provides the following optimized restrictions and improvements.

In a class of this embodiment, a guide channel is provided on a surface of a base of the first water throughflow block to guide excess water to discharge.

In a class of this embodiment, the optical waveguide as a whole is a cylinder, a frustum of a cone, a prism, or a frustum of a prism.

In a class of this embodiment, the contact window is made of sapphire, K9 glass, quartz glass or diamond; the optical waveguide is made of sapphire, K9 glass, or diamond.

In a class of this embodiment, the contact window and the optical waveguide are an integrated structure of sapphire.

In a class of this embodiment, the contact window and foreparts of the cooling blocks present a boss structure as a whole.

In a class of this embodiment, liquid cooling channels of the first water throughflow block and the second water throughflow block are connected in series or are independent from each other.

In a class of this embodiment, the cooling blocks are made of copper, aluminum, iron, gold-plated copper, gold-plated aluminum, stainless steel or diamond.

In a class of this embodiment, the first water throughflow block and the second water throughflow block are made of copper, aluminum, stainless steel, hard anodized aluminum or plastic.

In a class of this embodiment, the semiconductor lasers each comprise bar chips packaged on a heat sink, and the heat sink is a micro-channel heat sink, a macro-channel heat sink or a metal block; the bar chips comprise a single luminous point or a plurality of luminous points.

In a class of this embodiment, a collimating lens is disposed in front of the semiconductor lasers for fast axis collimation or for fast and slow axis collimation simultaneously.

In a class of this embodiment, in the presence of the collimating lens disposed in front of the semiconductor lasers for fast axis collimation or for fast and slow axis collimation simultaneously, the optical waveguide is replaced by a pair of light barriers which are perpendicular to the slow axis and are plated with high-reflective films on inner sides thereof In a class of this embodiment, the light barriers are made of gold-plated copper or silver-plated copper.

Advantages of the bilateral cooling type semiconductor laser system of the invention are summarized as follows.

1. The divergence angle of the bars along the fast axis in the semiconductor laser array is between 30 and 40 degrees, and the divergence angle along the slow axis is between 5 and 10 degrees. Employing the optical waveguide to transmit laser can restrict the divergence of the laser beams. The beams are reflected repeatedly in the optical waveguide to form uniform light spots in the end.

2. The coolers of the system feature unique, compact and stable structure, so that the temperature of the working end surface thereof adapted to direct contact with skin can be close to freezing point.

3. The thermoelectric coolers (TEC) are used as a cooling source to adjust the temperature of the cooling blocks and cool the contact window. The temperature of the contact window can drop to 5 degrees Celsuis (freezing point), thereby effectively alleviating the pain during treatment.

4. The water throughflow blocks are equipped with liquid cooling channels thereby having high heat dissipation efficiency. In addition, the water throughflow block below the thermoelectric coolers is in series connection to the liquid cooling channels of the semiconductor laser array, so that the cooling water paths of the semiconductor laser array and the thermoelectric coolers (TEC) are connected in series and communicate with one another via the water throughflow blocks, presenting a simple structure. As a result, the problem of the disconnection of branches of conventional parallel connected water paths is solved, the semiconductor laser can be cooled effectively, and the operation of the laser is stable and reliable.

5. The contact window is designed as a boss structure, which precludes the interference of auxiliaries such as cooling gel in the process of treatment, thereby ensuring the stable and reliable operation of the laser. The contact window is convenient for replacement, and close contacts the skin in use, the temperature of the contact site is close to freezing point, which effectively protects the skin from heat injury and pain, and increases the treatment energy and improves the therapeutic effectiveness. In use, the contact window presses the skin and flattens the hair follicle, so that the absorption rate of the laser is increased by 30-40%.

6. The guide channel is provided on the water throughflow block so that excess water resulting from moisture condensation can be discharged, thereby avoiding the pollution of the laser semiconductor.

7. A collimating lens (mainly for fast axis collimation) is disposed in front of the semiconductor lasers to narrow the divergence angle, and the optical waveguide can restrict the laser divergence along the slow axis. In the end, strip spots are produced at the outlet of the optical waveguide, and the energy density of each spot satisfies the requirement for laser medical treatment. Only by a single scanning can the same or even better effect be achieved compared to conventional repeated exposure in the uniform spots. Optionally, a pair of light barriers perpendicular to the slow axis are disposed in front of the light emitting surface of the semiconductor laser to restrict the beams along the slow axis.

Figure 1:
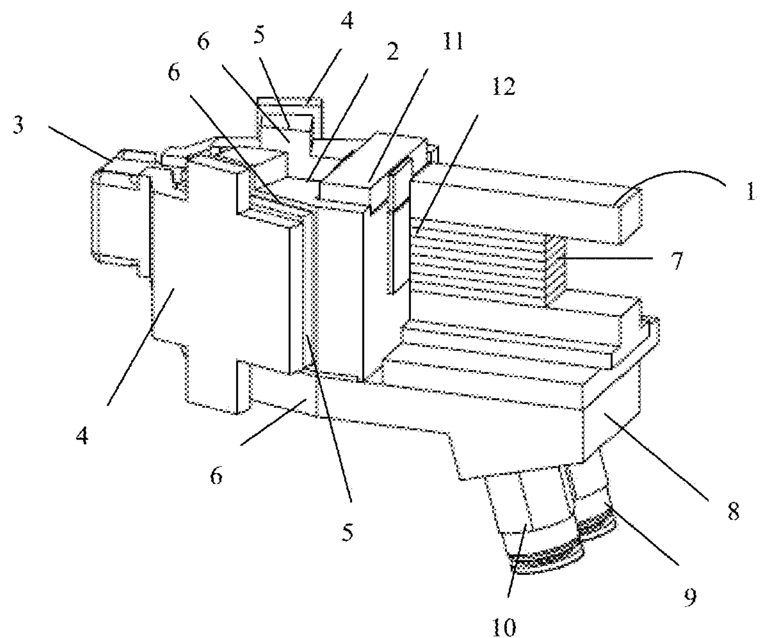
FIG. 1 is a stereogram of a bilateral cooling type semiconductor laser system in accordance with one embodiment of the invention.

In the drawings, the following reference numbers are used: 1. Semiconductor laser array; 2. Optical waveguide; 3. Contact window; 4. Cooling block; 5. Thermoelectric cooler (TEC); 6. First water throughflow block; 7. Heat sink; 8. Second water throughflow block; 9. Water inlet; 10. Water outlet; 11. Fixed block; 12. Bar chip (amounting site); 13. Collimating lens.

DETAILED DESCRIPTION OF THE EMBODIMENTS

Detailed description of the invention will be given below in conjunction with accompanying drawings.

Figure 2:
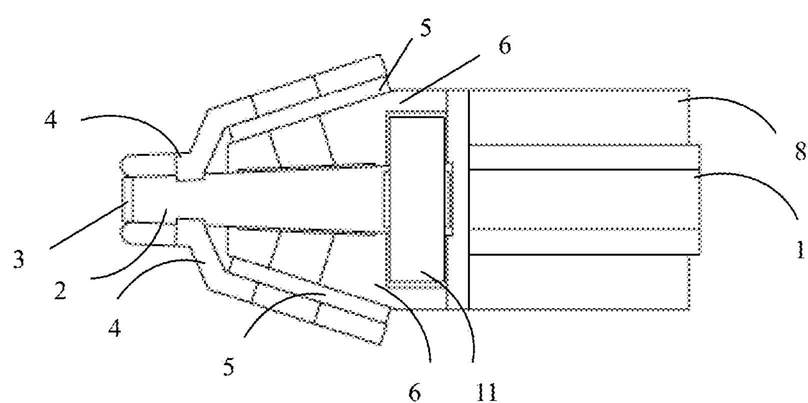
FIG. 2 is a top view of a bilateral cooling type semiconductor laser system in FIG. 1.

As shown in FIGS. 1 and 2, the invention provides a bilateral cooling type semiconductor laser system for medical beauty use, particularly for hair removal. The system comprises a semiconductor laser array 1, an optical waveguide 2, a contact window 3, cooling blocks 4, thermoelectric coolers (TEC) 5, a first water throughflow block 6 and a second water throughflow block 8.

The semiconductor laser array 1 employs eight 808 nm bar chips 12 having an output power of 120 W which are packaged in a micro-channel heat sink 7. The semiconductor laser array 1 is disposed on the second water throughflow block 8.

The optical waveguide 2 is disposed at the laser emitting end of the semiconductor laser array 1, and totally reflects and output the laser beams. The contact window 3 abuts against a light outlet end of the optical waveguide 2.

The first water throughflow block 6 comprises a base and a U-shaped head located on the base. The middle and rear parts of the optical waveguide 2 are embedded in the U-shaped head. A fixed block 11 is disposed on a corresponding part of the optical waveguide to tightly press and fix the optical waveguide 2. A gap is provided between the optical waveguide and side walls of the U-shaped head. A pair of thermoelectric coolers (TEC) and a pair of cooling blocks are sequentially and symmetrically disposed at outer sides of the U-shaped head. The pair of cooling blocks extends to a forepart of the optical waveguide and encircles side walls of the contact window and the forepart of the optical waveguide.

The arrangement of the cooling structure can be understood from another perspective. The first water throughflow blocks 6 are disposed at two sides of the optical waveguide 2, and the thermoelectric coolers (TEC) 5 are disposed at the outer sides of the two first water throughflow blocks 6. The two first water throughflow blocks 6 at the two sides of the optical waveguide 2 can be integrated. The fixed block 11 is disposed on and presses the optical waveguide. The cooling blocks 4 are disposed at the outer sides of the thermoelectric coolers (TEC) 5. The foreparts of the two cooling blocks 4 encircle the contact window 3 and cool the contact window 3.

To improve the energy density, the optical waveguide presents in the form of a frustum of a prism or a frustum of a cone with capacity of beam convergence. In practice, if the optical waveguide is a metal, it should be hollow, and the four inner sides thereof should be plated with reflective films. Optionally, the optical waveguide can be made of transparent material, such as glass, resin, sapphire and diamond, which can be solid or hollow. Preferably, the optical waveguide is made of sapphire, K9 glass, or diamond.

The contact window and the optical waveguide are an integrated structure, preferably, made of sapphire. Most of the laser energy is constrained and transmitted in the optical waveguide and cannot spill over.

Preferably, the contact window and foreparts of the cooling blocks present a boss structure as a whole. The cooling blocks 4 are made of materials with high heat conductivity, such as copper, aluminum, iron, gold-plated copper, gold-plated aluminum, stainless steel or diamond.

The first water throughflow blocks 6 and the second water throughflow blocks 8 are formed independently in space, both made of copper, and a plurality of liquid cooling channels are disposed in the middle thereof. In addition, a guide channel is provided on a surface of a base of the first water throughflow blocks to guide excess water to discharge.

The cooling water path of the semiconductor laser array 1, i.e., the second water throughflow blocks 8, and the cooling water path of the thermoelectric coolers (TEC) 5, i.e., the first water throughflow blocks, are connected in series. In the second water throughflow blocks 8, water flows in from the water inlet 9, passes through the semiconductor laser array 1, reaches the two first water throughflow blocks 6, and flows out from the water outlet 10.

Optionally, to facilitate the processing, the liquid cooling channels of the first water throughflow blocks and the second water throughflow blocks are connected in series or are independent from each other.

In this example, at the working end surface of the contact window 3, the output power of the laser can reach 787.2 W, the temperature of the contact window can be less than 5 degrees Celsius, and the produced light spots are uniform.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

Figure 3:
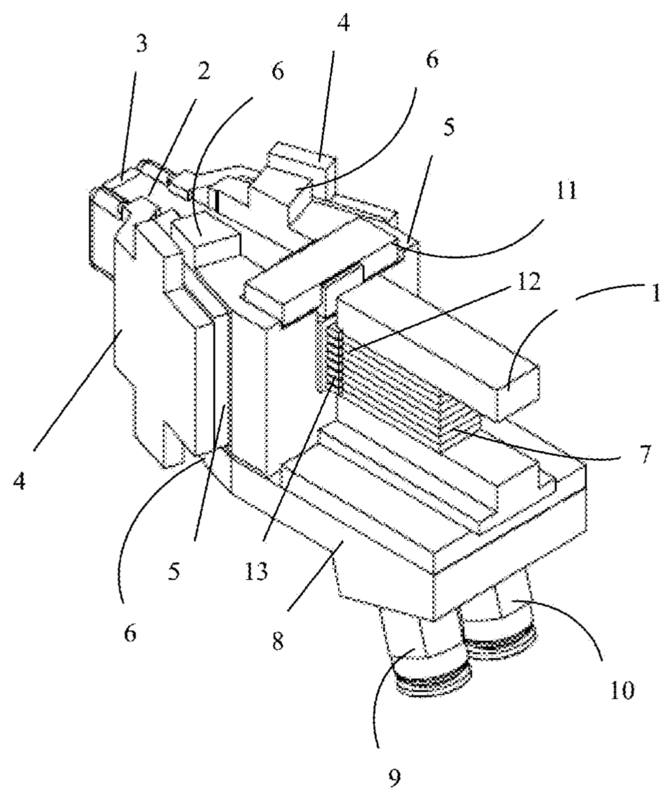
FIG. 3 is a stereogram of a bilateral cooling type semiconductor laser system equipped with a collimating lens in accordance with one embodiment of the invention.
Figure 4:
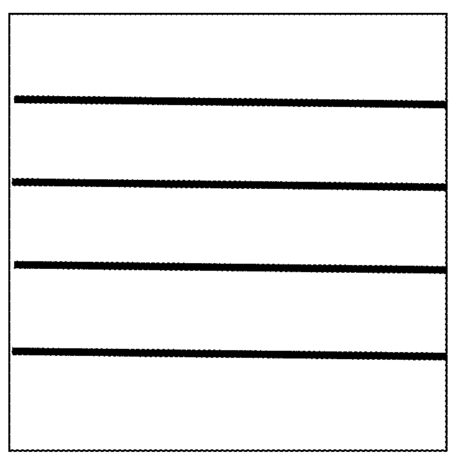
FIG. 4 is a schematic diagram of light spots in accordance with one embodiment of the invention.

Furthermore, as shown in FIG. 3, as needed, a collimating lens 13 is disposed in front of the semiconductor lasers for fast axis collimation or for fast and slow axis collimation simultaneously. As a result, strip spots are generated in the outlet of the optical waveguide (as shown in FIG. 4). The energy density of each strip spot can satisfy the medical requirements. Only by a single scanning can the same or even better effect be achieved compared to conventional repeated exposure in the uniform spots.

In the presence of the collimating lens 13, the optical waveguide can be replaced by a pair of light barriers which are perpendicular to the slow axis and are plated with high-reflective films on inner sides thereof, so that the divergence from the slow axis is prevented. The light barriers are made of gold-plated copper or silver-plated copper.

The invention claimed is:

1. A bilateral cooling type semiconductor laser system for medical beauty use, comprising:

a semiconductor laser array comprising a plurality of stacked semiconductor lasers, an optical waveguide disposed in front of a light emitting surface of the semiconductor laser array, a transparent contact window abutting against a light outlet end of the optical waveguide, a pair of cooling blocks for conduction cooling of the contact window, and a first water throughflow block;

wherein, the semiconductor laser array is disposed on the second water throughflow block and an insulating barrier is disposed therebetween;

the first water throughflow block comprises a base and a U-shaped head located on the base; middle and rear parts of the optical waveguide are embedded in the U-shaped head; a fixed block is disposed on a corresponding part of the optical waveguide to tightly press and fix the optical waveguide;

a gap is provided between the optical waveguide and side walls of the U-shaped head; a pair of thermoelectric coolers and a pair of cooling blocks are sequentially and symmetrically disposed at outer sides of the U-shaped head; the pair of cooling blocks extends to a forepart of the optical waveguide and encircles side walls of the contact window and the forepart of the optical waveguide.

2. The system of claim 1, wherein a guide channel is provided on a surface of a base of the first water throughflow block to guide excess water to discharge.

3. The system of claim 1, wherein the optical waveguide as a whole is a prism or a frustum of a prism.

4. The system of claim 1, wherein the contact window is made of sapphire, K9 glass, quartz glass or diamond; the optical waveguide is made of sapphire, K9 glass, or diamond.

5. The system of claim 1, wherein the contact window and the optical waveguide are an integrated structure of sapphire.

6. The system of claim 1, wherein the contact window and foreparts of the cooling blocks present a boss structure as a whole.

7. The system of claim 1, wherein liquid cooling channels of the first water throughflow block and the second water throughflow block are connected in series or are independent from each other.

8. The system of claim 1, wherein the cooling blocks are made of copper, aluminum, iron, gold-plated copper, gold-plated aluminum, stainless steel or diamond.

9. The system of claim 1, wherein the first water throughflow block and the second water throughflow block are made of copper, aluminum, stainless steel, hard anodized aluminum or plastic.

10. The system of claim 1, wherein the semiconductor lasers each comprise bar chips packaged on a heat sink, and the heat sink is a micro-channel heat sink, a macro-channel heat sink or a metal block; the bar chips comprise a single luminous point or a plurality of luminous points.

11. The system of claim 1, wherein a collimating lens is disposed in front of the semiconductor lasers for fast axis collimation or for fast and slow axis collimation simultaneously.

12. The system of claim 11, wherein the optical waveguide is replaced by a pair of light barriers which are perpendicular to the slow axis and are plated with high-reflective films on inner sides thereof.

13. The system of claim 12, wherein the light barriers are made of gold-plated copper or silver-plated copper.

* * * * *